(12) United States Patent
Hawley (10) Patent No.: US 10,925,741 B2
(45) Date of Patent: Feb. 23, 2021

(54) APPARATUS AND METHOD FOR PRODUCING AUGMENTIVE PRODUCTS

(71) Applicant: Michael John Hawley, Clear Lake, SD (US)

(72) Inventor: Michael John Hawley, Clear Lake, SD (US)

(73) Assignee: Michael John Hawley, Clear Lake, SD (US)

( * ) Notice: Subject to any disclaimer, the term of this patent is extended or adjusted under 35 U.S.C. 154(b) by 365 days.

(21) Appl. No.: 15/639,349

(22) Filed: Jun. 30, 2017

(65) Prior Publication Data

US 2018/0000596 A1 Jan. 4, 2018

Related U.S. Application Data

(60) Provisional application No. 62/357,475, filed on Jul. 1, 2016.

(51) Int. Cl.
*A61F 2/30* (2006.01)
*A61C 8/02* (2006.01)
(Continued)

(52) U.S. Cl.
CPC ........ *A61F 2/30965* (2013.01); *A61C 8/0006* (2013.01); *A61F 2/2803* (2013.01);
(Continued)

(58) Field of Classification Search
CPC ................ A61F 2/30965; A61F 2/2803; A61F 2310/00377; A61M 1/38; A61K 38/36;
(Continued)

(56) References Cited

U.S. PATENT DOCUMENTS

| 2002/0008063 A1* | 1/2002 | Zuk, Jr. ............... | A61M 1/3633 |
| | | | 210/435 |
| 2011/0034851 A1* | 2/2011 | Pierce ................. | A61L 27/3616 |
| | | | 604/6.01 |
| 2014/0121640 A1* | 5/2014 | Evans ................. | A61L 26/0057 |
| | | | 604/509 |

FOREIGN PATENT DOCUMENTS

WO WO-2016015754 A1 * 2/2016 ........... A61L 27/225

OTHER PUBLICATIONS

"Medical Design Sialkot: PRF Box Platelet Rich Fibrin", "Medical Design Sialkot: PRF Box Platelet Rich Fibrin", retrieved on Jun. 30, 2017, URL: http://medicaldesignpk.tradekorea.com/product/detail/13602174/PRF-BOX-PLATELET-RICH-FIBRIN.html?minisiteprodgroupno=55983, 4 pp.
(Continued)

*Primary Examiner* — Michael M. Robinson
(74) *Attorney, Agent, or Firm* — Billion & Armitage (57) ABSTRACT

An apparatus for shaping a Platelet Rich Fibrin component of patient whole blood includes a main body. The main body includes a substantially planar surface. The main body also has a reservoir positioned therein. The substantially planar surface includes a plurality of channels fluidly connecting the substantially planar surface and the reservoir. The apparatus also includes a lid which is positioned over the substantially planar surface. The lid is used to compress a Platelet Rich Fibrin component. Liquids that are expressed from the Platelet Rich Fibrin component flow to the reservoir. The apparatus also includes openings for forming plugs of Platelet Rich Fibrin material.

19 Claims, 6 Drawing Sheets

(51) Int. Cl.
  *A61F 2/28* (2006.01)
  *A61L 27/22* (2006.01)
  *A61L 24/10* (2006.01)
  *A61L 26/00* (2006.01)
  *A61K 38/36* (2006.01)
  *A61M 1/38* (2006.01)

(52) U.S. Cl.
  CPC ............ *A61K 38/36* (2013.01); *A61K 38/363* (2013.01); *A61L 24/106* (2013.01); *A61L 26/0042* (2013.01); *A61L 27/225* (2013.01); *A61M 1/38* (2013.01); *A61F 2310/00377* (2013.01); *B01L 2300/0861* (2013.01); *Y10S 514/802* (2013.01)

(58) Field of Classification Search
  CPC .. A61L 26/0042; A61L 24/106; A61L 27/225; A61C 8/0006; B01L 2300/0861; Y10S 514/802
  See application file for complete search history.

(56) References Cited

OTHER PUBLICATIONS

Angerame, et al., "Application of platelet-rich fibrin in endodontic surgery: a pilot study", Angerame et al., "Applicatoin of platelet-rich fibrin in endodontic surgery: a pilot study", ScienceDirect, Jun. 30, 2015, 51 pp.

\* cited by examiner

APPARATUS AND METHOD FOR PRODUCING AUGMENTIVE PRODUCTS

RELATED APPLICATIONS

This application claims the benefit under 35 U.S.C. § 119(e) of U.S. Provisional Patent Application No. 62/357,475 filed Jul. 1, 2016, which is incorporated herein by reference. A claim of priority is made.

TECHNICAL FIELD

Various embodiments described herein relate to an apparatus for producing augmentive products and a method for making the augmentive product using the apparatus. More specifically, the apparatus and method are used for various types of dentistry.

BACKGROUND

Dental surgeries including tooth extractions, implant placement, bone grafting and others. More recently, dentists have started to rely on augmentative products and the methods for making these products as part of these surgeries. The use of augmentative products and methods help patients. Among the benefits is that the use of augmentative products and methods speed a patient's healing.

BRIEF DESCRIPTION OF THE DRAWINGS

The embodiments will be readily understood by the following detailed description in conjunction with the accompanying drawings, wherein like reference numerals designate like structural elements, and in which.

DETAILED DESCRIPTION

In the following paper, numerous specific details are set forth to provide a thorough understanding of the concepts underlying the described embodiments. It will be apparent, however, to one skilled in the art that the described embodiments may be practiced without some or all of these specific details. In other instances, well known process steps have not been described in detail in order to avoid unnecessarily obscuring the underlying concepts.

This apparatus is intended for use in the dental surgical industry in both surgical specialties and general practice. Applications include, but are not limited to, implants, apical surgeries, extractions, and bone and tissue grafting in support of general oral surgery. The apparatus fabricates products that aid in healing. The apparatus will be used for fashioning tissue membranes or cylindrical slugs derived via phlebotomy procedure from the patient's centrifuged whole blood.

Dental surgeries including tooth extractions, implant placement, bone grafting and others. Dentists have begun to rely on augmentative products to speed healing. In one embodiment, autologous blood (i.e., blood emanating from the patient himself) is placed in a centrifuge. The autologous blood is spun to separate components that effectuate better healing. That portion of the patient whole blood functioning in this capacity is the Platelet Rich Fibrin ("PRF") component. This element contains platelets and fibrin, which initiate clot formation and promote maturation elements to enable stabilization. This portion also contains agents that actually recruit and promote healing cells and molecules from the blood and tissue. By using these PRF constituents, the practitioner can fabricate both membranes (to cover grafts) and plugs (to press into bony defects). This, in turn, both improves and accelerates the healing process once a surgical procedure is concluded.

Figure 1:
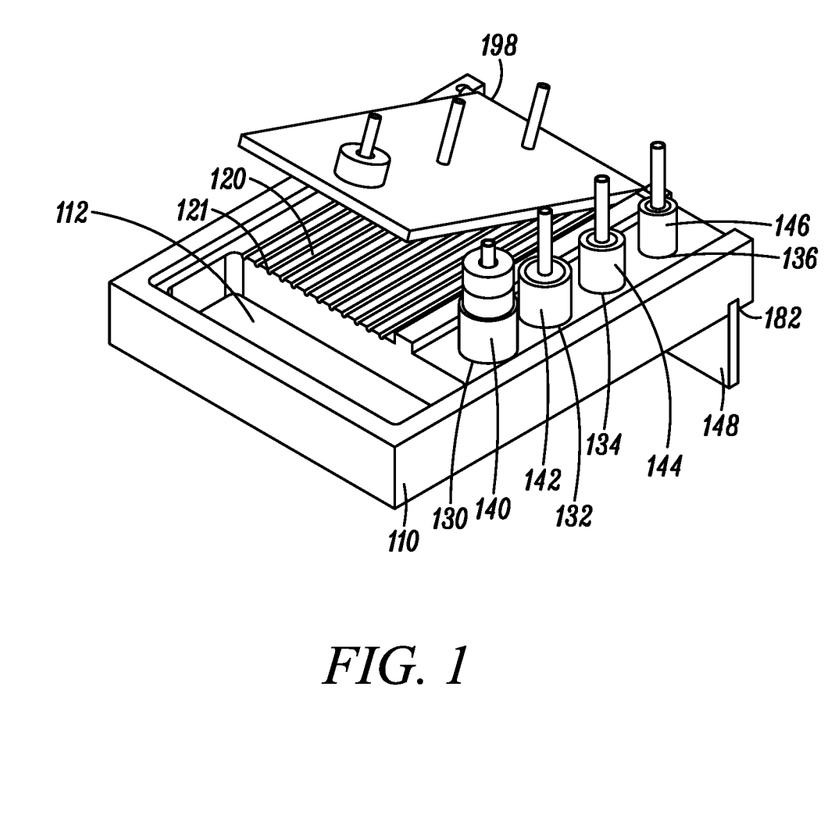
FIG. 1 is a perspective view of an apparatus for shaping a Platelet Rich Fibrin (PRF) component of patient whole blood into sheets and plugs of varying sizes, according to an example embodiment.
Figure 2:
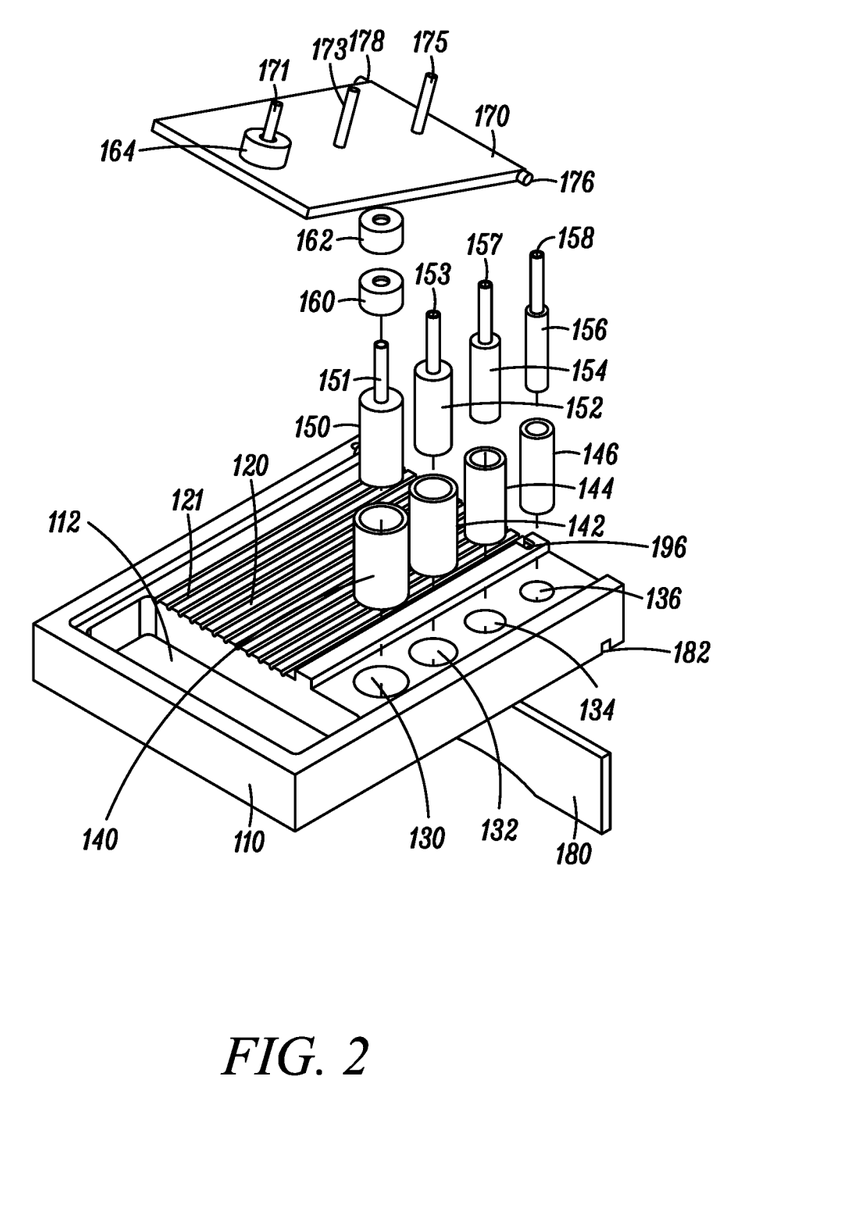
FIG. 2 is an exploded perspective view of an apparatus for shaping a Platelet Rich Fibrin (PRF) component of patient whole blood into sheets and plugs of varying sizes, according to an example embodiment.

FIG. 1 is a perspective view of an apparatus 100 for shaping a Platelet Rich Fibrin component of patient whole blood into sheets and plugs of varying sizes, according to an example embodiment. FIG. 2 is a perspective exploded view of an apparatus 100 for shaping a Platelet Rich Fibrin component of patient whole blood into sheets and plugs of varying sizes, according to an example embodiment. The apparatus 100 includes a main body 110. The main body 110 includes a grooved surface 120 that is substantially planar absent the grooves 121. The main body also includes a reservoir 112 at one end of the main body 110. At least some of the grooves are connected or fluidly coupled t the reservoir 112. The grooves are sized to allow fluids associated with a Platelet Rich Fibrin component to flow through the grooves 121. The main body 100 also includes at least one cylindrical opening 130. As shown in FIGS. 1 and 2, the main body includes four cylindrical openings 130, 132, 134, 136. The cylindrical openings 130, 132, 134, 136, may have the same diameter or different diameters. In some embodiments, one or more cylinders can be of equal diameter and size. In another embodiment, each of the cylinders 130, 132, 134, 136 can have different diameters and be of different sizes. It should be noted that in FIGS. 1 and 2, there are four cylindrical openings but in other embodiments, there may be more openings or less openings.

At least some of the cylindrical openings 130, 132, 134, 136 receive a cylinder or sleeve 140, 142, 144, 146. As shown in FIGS. 1 and 2, each cylindrical opening 130, 132, 134, 136 receives a sleeve 140, 142, 144, 146. As shown in FIG. 2, the sleeves 140, 142, 144, 146 each have a wall thickness that is about equal. It is contemplated that some of the cylindrical openings can have sleeves with the same outer diameter to fit within a cylindrical opening, but with different inner diameters. In this way a sleeve could be changed out to form a smaller diameter opening or space.

Also associated with the apparatus are a set of pistons 150, 152, 154, 156. Each of the pistons 150, 152, 154, 156 has an outside diameter that is substantially equal to the inner diameter of the corresponding sleeve 140, 142, 144, 146. The pistons have piston rods 151, 153, 155, 157. The piston rods 151, 153, 155, 157 are sized so that they can bear a doughnut-shaped weight. The piston rods 151, 153, 155, 157 are also attached to the pistons 150, 152, 154, 156 so that they can be pushed or pulled without separating from the pistons 150, 152, 154, 156. Doughnut shaped weights 160, 162, 164 are also shown in FIGS. 1 and 2. Weights 160, 162 are placed on piston rod 150. The apparatus 100 for shaping a Platelet Rich Fibrin component of patient whole blood into sheets and plugs of varying sizes 100 also includes a lid 170. The lid 170 covers at least the grooved surface 120 of the main housing 110. The lid 170 is also a weight that is used to compress or express liquid from the Platelet Rich Fibrin component. The lid includes posts 171, 173, 175 which is on the exterior surface of the lid 170. Weights, such as weight 164 can be placed on a post 171, 173, 175 to further load the lid and increase the force on the Platelet Rich Fibrin component. It should be noted that only three weights are shown in FIGS. 1 and 2 and that there could be many more that are used to weight the plate 170 and the pistons 150, 152, 152, 156. In other words, it is contemplated that multiple weights could be placed on each post or each piston rod in some applications of this apparatus.

The apparatus 100 for shaping a Platelet Rich Fibrin component of patient whole blood into sheets and plugs of varying sizes also includes a table stand 180 which lifts one edge of the body 110 and imparts a tilt to the surface 120. The body 110 of the table assembly includes a slot or groove 182 sized to receive the edge of the table stand 180. The table stand 180, in this embodiment, is a thin piece of material, such as metal. The edge of the table stand 180 is placed into the groove 182 to impart a tilt on the entire table apparatus 100. The tilt that results directs the flow of fluids expressed from the Platelet Rich Fibrin components to flow downhill in the grooves, such as groove 121, of the surface 120. The fluids flow to the reservoir 112 and collect there.

Figure 3:
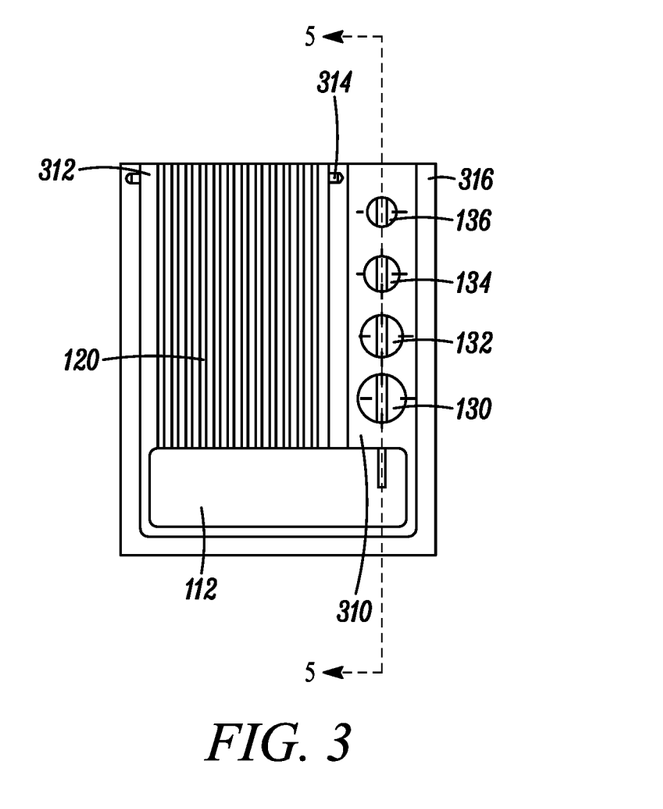
FIG. 3 is a top view of the body or table of the apparatus for shaping a Platelet Rich Fibrin component of patient whole blood into sheets and plugs of varying sizes, according to an example embodiment.
Figure 4:
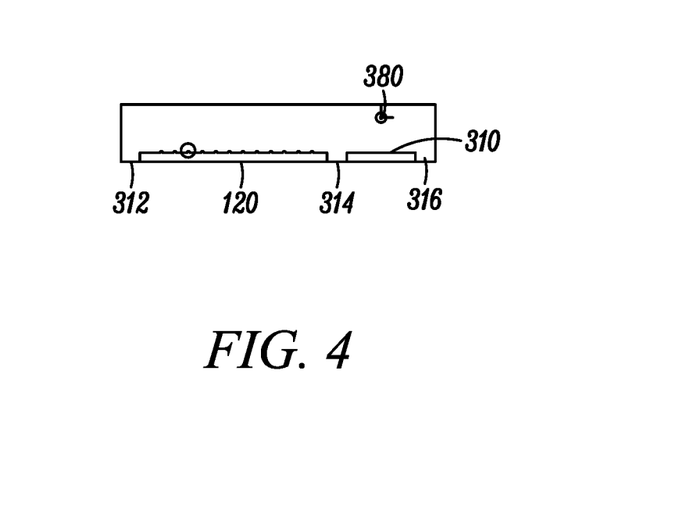
FIG. 4 is an end view of the body or table of the apparatus for shaping a Platelet Rich Fibrin component of patient whole blood into sheets and plugs of varying sizes, according to an example embodiment.

FIG. 3 is a top view of the body 110 or table of the apparatus 100 for shaping a Platelet Rich Fibrin component of patient whole blood into sheets and plugs of varying sizes, according to an example embodiment. FIG. 4 is an end view of the body 110 or table of the apparatus 100 for shaping a Platelet Rich Fibrin component of patient whole blood into sheets and plugs of varying sizes, according to an example embodiment. Now referring to both FIGS. 3 and 4, the body 110 or table of the apparatus 100 will be further detailed. The grooved surface 120 and the area 310 surrounding the cylinders 130, 132, 134, 136 are slightly recessed from the surface which forms the outer edge of the body 110 or table. The recesses 120 and 310 in the body form a first rail 312, a second rail 314 and a third rail 316. The first rail 312 and the third rail 316 correspond with the outer perimeter of the table or body 110. The outer perimeter of the body 110 is bound on three sides. A side that is normally elevated while in use is not bound. The second rail 314 is located between the first rail 312, and the third rail 316. The first rail 312, and the second rail 314 bound the grooved surface 120. The grooved surface 120 has grooves that run to the reservoir 112. The second rail 314 and the third rail 316 bound the area 310 surrounding the cylindrical openings 130, 132, 134, 136.

Figure 5:
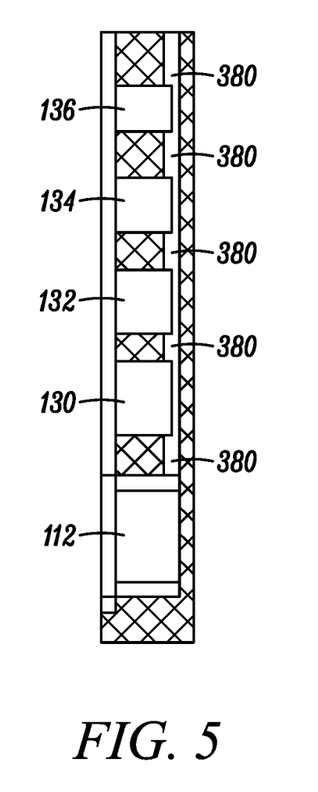
FIG. 5 is cross sectional view of the body or table of the apparatus for shaping a Platelet Rich Fibrin component of patient whole blood into sheets and plugs of varying sizes, as viewed along line 5-5 in FIG. 4, according to an example embodiment.

FIG. 5 is cross sectional view of the body 110 or table of the apparatus for shaping a Platelet Rich Fibrin component of patient whole blood into sheets and plugs of varying sizes, as viewed along line 5-5 in FIG. 4, according to an example embodiment. As shown in the cross-sectional view, the housing 110 includes a bored tunnel or bore 380 that fluidly couples the base of the cylindrical wells or cylindrical openings 130, 132, 134, 136 and the sump or reservoir 112. The cross-sectional view of FIG. 5 details the size and position of the bore 380 that fluidly connects these portions of the base 110. The bore and the base of each of the cylindrical openings are positioned so as to minimize fluid from collecting in either the cylindrical openings 130, 132, 134, 136 or the bore 380.

In operation, the apparatus 100 is used to shape the harvested PRF component of patient whole blood after it is centrifuged into sheets and plugs of varying sizes. The sheets and plugs can then be used in dental surgery and potentially other surgery. Dental surgeries include tooth extractions, implant placement, bone grafting and others. Dentists rely on augmentative products, that is made from the patient's blood, and the methods for making these products as part of these surgeries. The use of augmentative products and methods speed a patient's healing because there are no rejection issues.

After centrifugation, the PRF portion will begin to clot and hold together and can then be removed in whole as an amorphous mass and manipulated. The apparatus 100 assists fabrication into either of two general shapes, a sheet (membrane) or a cylindrical form (plug). To form a sheet of material, the amorphous mass is placed on the surface 112. The lid 170 is placed over the amorphous mass and compressed into a sheet. Weights, such as weight 164, can be added to the sheet to produce additional force to be placed on the sheet during formation. The number of weights that can be used can be placed on posts 171, 173, 175. The downward force of the lid 170 and any additional weight placed thereon, compresses the amorphous mass into a sheet. Portions of the amorphous mass can also be placed into the openings 130, 132, 134, 138. Pistons, 150, 152, 154, 158 are placed onto the portions of amorphous mass. The pistons 150, 152, 154, 158 have piston rods 151, 153, 155, 157 sized to receive one or more weights. The piston, piston rod, and weight place a downward force on the amorphous mass in the cylindrical opening 130, 132, 134, 138 to form a plug to be used in various sorts of operations.

In both instances, the weight compresses the amorphous mass that s either placed on the flat surface or in the cylindrical opening. During compression into either form, the tissue liquid that remains in the PRF is expressed out of the mass and drains either down the bored tunnel or bore 380 at the base of the cylindrical openings 130, 132, 134, 136 or wells, or down the V-shaped grooves on the surface 120 of the table apparatus 100. The table body 110 is inclined or tilted when the table stand 180 is placed into groove or slot 182. The incline of the table body 110 is sufficient for gravity to pull the tissue fluids expressed from the process downslope into the collection well or sump or reservoir 112.

This apparatus differs in design from other apparatuses currently in use in that the apparatus 100 uses the slope of the inclined plane to drain the excess tissue fluids into a well or sump or reservoir 112, away from the PRF membrane or plugs that are forming.

Advantageously, the apparatus 100 for shaping a Platelet Rich Fibrin component of patient whole blood into sheets and plugs of varying sizes includes many key functions in one station. Another apparatus utilizes a perforation tray through which the excess fluid drips into a pan below. The perforation tray must be removed to gain access to the fluid expressed from the Platelet Rich Fibrin component. In some operations, the fluid express from the Platelet Rich Fibrin component is mixed with other constituents to form other components that are used ins some operations. For example, bone chips may be ground into a powdery consistency. The fluid expressed from the Platelet Rich Fibrin component can be mixed with the powdery substance to form another useful component for various operations. This can be used to promote bone development where needed. This apparatus does not require the removal of various components to gain access to this fluid. The apparatus 100 delivers the fluid to the reservoir 112 so that it can be accessed at the reservoir. No need to tilt a separate pan to obtain some of the fluid expressed from the Platelet Rich Fibrin component. Still another advantage is to allow for several plug sizes. The apparatus 100 offers a choice of four (4) different diameters from which the practitioner can select depending on surgical needs. It is contemplated that the sleeves could be fashioned to provide still other sizes. In addition, the sleeves could also be provided to allow production of plugs of approximately the same size from the body 110 of the apparatus 100.

For assembly, the table stand 180 is inserted into the slot or groove 182 on the bottom surface of the table body 110. This provides a slope to the table body 110, the surface 120 and the bore 380 to enable liquid from the Platelet Rich Fibrin component to run down the grooves on the table body surface 120 and into the well or sump or reservoir 112 at the down-slope edge of the table body 110. The lid assembly 170 is then put in place with the pins 176, 178 at an upper end of the lid 170 engaging with the machined pin slots 196, 198 on the up-slope end of the table body 110. Cylindrical weights, such as weight 164, can be added to the shafts on the top side of the lid 170 to produce additional force on the lid 170 which in turn increases the pressure (force per unit area) on the Platelet Rich Fibrin component positioned between the grooved surface 120 and the lid 170.

As shown in FIGS. 1 and 2, sized pistons fit within four similarly sized cylindrical openings. Four different diameter sizes are shown in FIGS. 1-3 and 5. It is contemplated that the number of different sized openings can be provided. In one embodiment, a sleeve 140 is inserted into the corresponding well or cylindrical opening 130 in the table body 110. Next, the centrifuged clot is placed in the sleeve 140, followed by the piston 150 for compression. Weights 160, 162 can also be added to the piston 150 to increase pressure on the material within the walls of the sleeves or cylindrical opening 130. The same can be done for the other cylindrical openings, sleeves and pistons already described, as desired by the operator. Machined into the base of the wells in the table body 110 is a bore-hole channel or bore 380 that runs from the up-slope end of the table body 110, through the base of each of the wells or cylindrical bodies 130, 132, 134, 136 and into the well/sump or reservoir 112 at the downslope end of the table 100. This provides a drainage channel for liquid that will be compressed out of the material in the piston/cylinder apparatus. See FIG. 5 and the related description above for bore hole location and direction.

Figure 6:
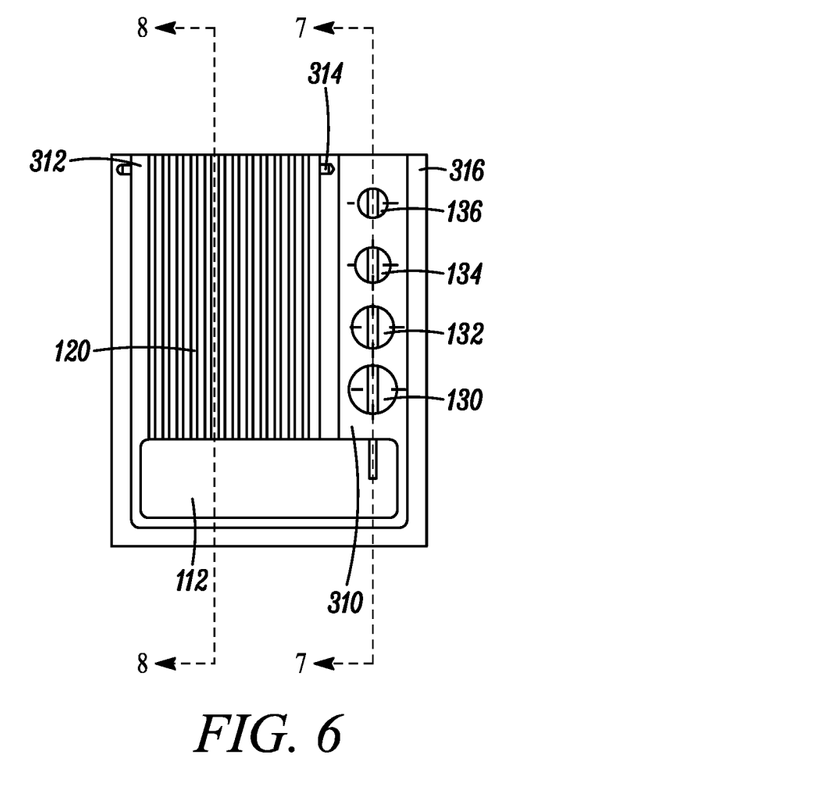
FIG. 6 is a top view of the body or table of the apparatus for shaping a Platelet Rich Fibrin component of patient whole blood into sheets and plugs of varying sizes, according to an example embodiment.

FIG. 6 is a top view of the body or table of the apparatus for shaping a Platelet Rich Fibrin component of patient whole blood into sheets and plugs of varying sizes, according to an example embodiment.

Figure 7:
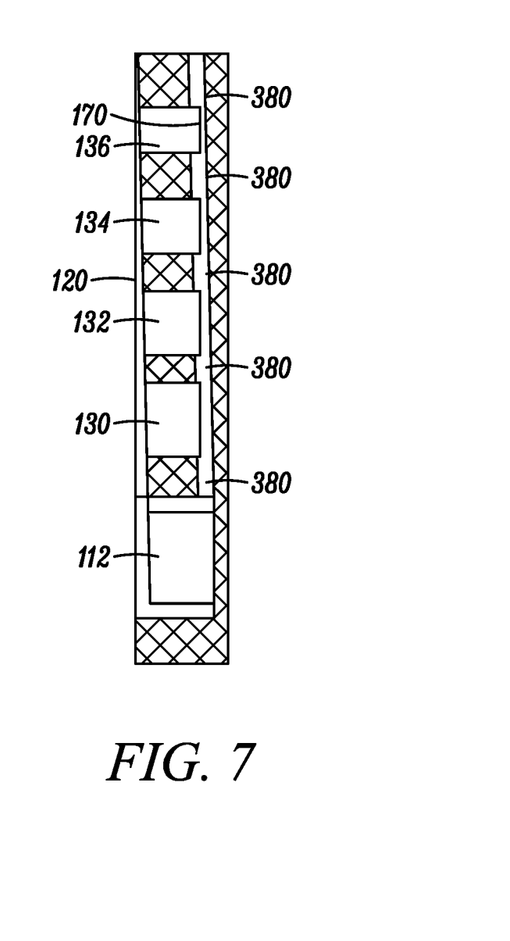
FIG. 7 is cross sectional view of the body or table of the apparatus for shaping a Platelet Rich Fibrin component of patient whole blood into sheets and plugs of varying sizes, as viewed along line 7-7 in FIG. 6, according to an example embodiment.

FIG. 7 is cross sectional view of the body or table of the apparatus for shaping a Platelet Rich Fibrin component of patient whole blood into sheets and plugs of varying sizes, as viewed along line 7-7 in FIG. 6, according to an example embodiment.

Figure 8:
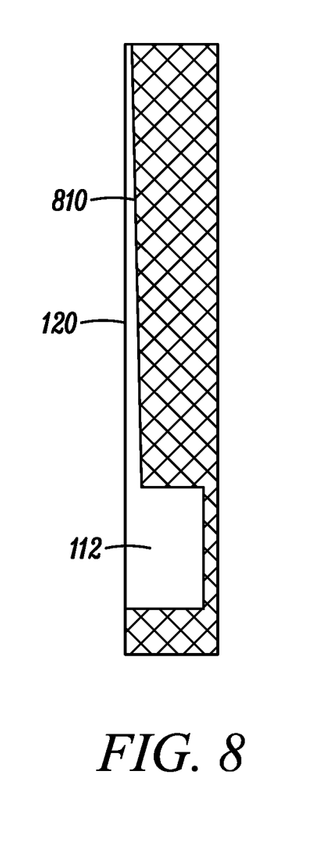
FIG. 8 is cross sectional view of the body or table of the apparatus for shaping a Platelet Rich Fibrin component of patient whole blood into sheets and plugs of varying sizes, as viewed along line 8-8 in FIG. 6, according to an example embodiment.

FIG. 8 is cross sectional view of the body or table of the apparatus for shaping a Platelet Rich Fibrin component of patient whole blood into sheets and plugs of varying sizes, as viewed along line 8-8 in FIG. 6, according to an example embodiment.

Now referring to FIGS. 6-8, it can be seen that at least one of the channels and the bore 380 is sloped with respect to the substantially top planar surface of the body 110 of the apparatus 100.

In summary, PRF clots are removed from a centrifuge and placed either on the table or surface 120 or in any of the cylindrical openings 130, 132, 134, 136 or wells having the sleeves 140, 142, 144, 146 already inserted. PRF is placed on the surface 120 if a sheet of augmentive material is required and in a cylindrical opening 130, 132, 134, 136 or well if a plug is required. The cylindrical opening 130, 132, 134, 136 or well selected depends on the size and shape of the desired tissue product. The lid 170 or piston associated with a cylindrical opening is then applied. Gravity compresses the portion of PRF material to form a cylindrical mass of a certain size (in the case of the cylinders) or a flat sheet (in the case of the grooved table). The apparatus 100 is inclined when the table stand 180 is inserted or engaged with the groove 182 in the body 110 of the apparatus 100. The resulting sloped plane aids with drainage channels (in the case of the grooved table) or a drainage tunnel (in the case of cylindrical slugs) that permits the fluid supernatant from either product (sheet or cylinder) to flow downward into the collection sump or reservoir 112. Fluid collected in this way can be reserved in any fashion for further use in preserving, rehydrating or maintaining hydration of the fabricated products. The table stand 180 supplied with the table 110, when placed in the receiver position on the back of the table 110 provides the slope for the inclined plane. After compression by the lid on the table or by the pistons in the sleeves/wells the membrane or cylindrical plug is ready for use in the surgical site. It may be either removed and immediately delivered to the surgical site or retained in the collection well/sump where the fluid collects.

The four cylindrical openings 130, 132, 134, 136 or wells, along with their sleeves and pistons, provide options for alternate plug product diameters depending on surgical needs. These vary upward from a 1-to-4.8 ratio (0.625 ranging up to 3.000). The sleeve and cylinder system is designed such that the height of the sleeve is situated sufficiently above the level of the table that it can be easily removed with the piston and product remaining in the sleeve. The product can then be expressed into the desired location by simply pushing on the stem of the piston and driving it through the sleeve to force out the PRF plug. This feature of this apparatus allows the formed product or products to be taken from the forming chamber and delivered directly to the surgical site or any other site.

The apparatus is also equipped with weights that fit onto stems mounted on the lid or on the piston stems themselves. This enables the user to vary the force applied to the PRE in order to influence desired thickness and density of the final product. This apparatus 100 is designed to have an inclined plane drainage system for fabricating PRF autogenous membranes and cylindrical slugs for use in dental implants and grafting. The design also acts as a delivery system for the formed cylindrical plugs using sleeves as carriers and pistons to express the product at the desired site.

An apparatus for shaping a Platelet Rich Fibrin component of patient whole blood includes a main body having a substantially planar surface. The main body has a reservoir positioned in the main body, and a plurality of channels fluidly connecting the substantially planar surface and the reservoir. In one embodiment, the substantially planar surface is inclined toward the reservoir. The apparatus further includes a table stand. The main body has a receiver for the table stand. When the table stand is placed in the receiver the main body inclines toward the reservoir. In one embodiment, the receiver is a groove within the main body and the table stand is a plate of material. It should be understood that the table stand could be of any geometric shape and the receiver could have a corresponding shape to receive the table stand. It is further contemplated that the table stand could be a block or even a plastic pad that could be placed under the main body at a point which would cause the main body to incline with the reservoir being the low point. The plurality of channels fluidly connect the substantially planar surface and the reservoir. In some embodiments, the floors of the plurality of channels can be inclined with respect to the substantially planar surface. The incline of the channels or channel floors is toward the reservoir to facilitate flow to the reservoir. The apparatus for shaping a Platelet Rich Fibrin component of patient can also include a lid. The lid covers at least a portion of the substantially planar surface. The lid places a load on a Platelet Rich Fibrin material. The lid is for forming a membrane of Platelet Rich Fibrin material. The amount of load can be altered. The apparatus also includes one or more lid weights. The lid includes a place for temporarily holding one or more lid weights. Thus, the load can be varied. The load may also be varied to vary the rate liquid is expressed from a sheet of Platelet Rich Fibrin material.

The main body and the lid can be hingedly connected. A hinge is located between the main body and the lid. In some embodiments, the lid is used to control the thickness of the platelet rich fibrin sheet. In such an embodiment, the hinge holds the lid at a distance from the substantially planar surface of the main body. The hinge can have a first hinge position for forming a membrane of a first thickness, and a second hinge position for forming a membrane of a second thickness. Basically, the hinge position and the load on the lid can be used to form membranes of varying thicknesses. It is contemplated, in one embodiment, that the main body of the apparatus could have a bracket with a plurality of spaced openings for receiving cylindrical pins attached to one end of the lid. In this way, the lid could be placed at any height with respect to the substantially planar surface. In still another embodiment, a bar with two hinge openings could be mechanically attached to the main body and the height of the bar could be adjusted to a range of desired heights.

The main body of the apparatus for shaping a Platelet Rich Fibrin can also include one or more openings for forming plugs of Platelet Rich Fibrin material. The apparatus also can one or more plug weights which fit within the one or more openings for forming plugs. In one embodiment, the one or more plug weights is piston-shaped with a cylindrical piston portion and a rod portion. The cylindrical piston portion fits within at least one of the one or more openings. The rod portion is sized to receive supplemental weights. The plug weights would be doughnut shaped so they could easily slip on the rod portion to add to the load on the material in one of the openings. In one embodiment, the apparatus also includes one or more sleeves sized to fit within the one or more openings for forming plugs. A plug of a first dimension can be formed in the opening when a first sleeve is positioned in the opening. A plug of a second, smaller dimension can be formed within a sleeve within an opening when a second sleeve is positioned within the opening. A plug of a third dimension could be formed in the opening without any sleeve. In another embodiment, the main body includes a plurality of different-sized openings for forming plugs of Platelet Rich Fibrin material having different dimensions. The apparatus for shaping a. Platelet Rich Fibrin component of patient whole blood wherein the main body includes one or more bores for the one or more openings for forming plugs of Platelet Rich Fibrin material. The one or more bores fluidly couple the one or more openings for forming plugs to the reservoir within the main body.

The reservoir of the apparatus for shaping a Platelet Rich Fibrin component of patient whole blood of is positioned so that fluid in the reservoir is accessible without having to move another portion of the apparatus. In other words, fluids expressed from the Platelet Rich Fibrin material can be accessed without having to remove components of the apparatus. More importantly, the membrane of Platelet Rich Fibrin can remain in place while the reservoir is accesses. Similarly, a plug or plugs do not have to be moved to access or remove fluid from the reservoir.

An apparatus for shaping a Platelet Rich Fibrin component of patient whole blood includes a main body with a substantially planar surface, a lid positionable above the main body, a lid weighting apparatus, at least one piston-shaped weight, and a supplement piston weight for temporarily adding weight to the piston-shaped weight. The main body has a fluid reservoir therein, a plurality of channels therein, at least one cylindrical opening therein and at least on bore therein for connecting the at least one cylindrical opening to the reservoir.

The plurality of channels fluidly connects the substantially planar surface and the reservoir. The piston-shaped weight has a cylindrical end sized to fit within the cylindrical opening in the main body. The lid is positionable above the plurality of channels in the main body. The apparatus also includes a supplemental piston weight for temporarily adding weight to the piston-shaped weight. Other weights can be added to the lid. In one embodiment, the lid can be positioned above the main body at a plurality of distances. In still another embodiment, the channels in the main body and the bores in the main body are in fluid communication with each other. The apparatus can also include a table stand removably attached to the main body. The table stand positioned to incline the main body and the channels and bores therein toward the reservoir in the main body.

The foregoing description, for purposes of explanation, used specific nomenclature to provide a thorough understanding of the invention. However, it will be apparent to one skilled in the art that the specific details are not required in order to practice the invention. Thus, the foregoing descriptions of specific embodiments of the present invention are presented for purposes of illustration and description. They are not intended to be exhaustive or to limit the invention to the precise forms disclosed. It will be apparent to one of ordinary skill in the art that many modifications and variations are possible in view of the above teachings.

The embodiments were chosen and described in order to best explain the principles of the invention and its practical applications, to thereby enable others skilled in the art to best utilize the invention and various embodiments with various modifications as are suited to the particular use contemplated. It is intended that the scope of the invention be defined by the following claims and their equivalents.

While the embodiments have been described in terms of several particular embodiments, there are alterations, permutations, and equivalents, which fall within the scope of these general concepts. It should also be noted that there are many alternative ways of implementing the methods and apparatuses of the present embodiments. It is therefore intended that the following appended claims be interpreted as including all such alterations, permutations, and equivalents as fall within the true spirit and scope of the described embodiments.

What is claimed:

1. An apparatus for shaping a Platelet Rich Fibrin component of patient whole blood comprising:
   a main body further comprising a substantially planar surface, the main body having or more openings therein for forming plugs of Platelet Rich Fibrin material;
   a lid for placing a force on the substantially planar surface of the main body, the lid for forming a membrane of Platelet Rich Fibrin material;
   at least one weight sized to fit within the one or more openings;
   a reservoir positioned in the main body;
   at least one bore fluidly connecting the one or more openings in the main body and the reservoir; and
   a plurality of channels fluidly connecting the substantially planar surface and the reservoir.

2. The apparatus for shaping a Platelet Rich Fibrin component of patient whole blood of claim 1 wherein the substantially planar surface is inclined toward the reservoir.

3. The apparatus for shaping a Platelet Rich Fibrin component of patient whole blood of claim 1 further comprising:
   at least one lid weight; and
   a plurality of weight receiving posts attached to the lid.

4. An apparatus for shaping a Platelet Rich Fibrin component of patient whole blood comprising:
   a main body further comprising a substantially planar surface;
   a reservoir positioned in the main body;
   a plurality of channels fluidly connecting the substantially planar surface and the reservoir;
   a lid which covers at least a portion of the substantially planar surface, the lid for forming a membrane of Platelet Rich Fibrin material; and
   a hinge between the main body and the lid.

5. The apparatus for shaping a Platelet Rich Fibrin component of patient whole blood of claim 4 further comprising a table stand, the main body having a receiver for the table stand positioned so that when the table stand engages the receiver, the main body inclines toward the reservoir.

6. The apparatus for shaping a Platelet Rich Fibrin component of patient whole blood of claim 4 wherein the plurality of channels fluidly connecting the substantially planar surface and the reservoir are inclined with respect to the substantially planar surface, the incline toward the reservoir.

7. The apparatus for shaping a Platelet Rich Fibrin component of patient whole blood of claim 4 further comprising one or more lid weights, wherein the lid includes a place for temporarily holding one or more lid weights.

8. The apparatus for shaping a Platelet Rich Fibrin component of patient whole blood of claim 4 wherein the hinge between the main body and the lid holds the lid at a distance from the substantially planar surface of the main body, the hinge including:
   a first hinge position for forming a membrane of a first thickness; and
   a second hinge position for forming a membrane of a second thickness.

9. The apparatus for shaping a Platelet Rich Fibrin component of patient whole blood of claim 4 wherein the main body includes one or more openings for forming plugs of Platelet Rich Fibrin material, the plugs of Platelet Rich Fibrin material having a diameter equal to the one or more openings for forming plugs.

10. The apparatus for shaping a Platelet Rich Fibrin component of patient whole blood of claim 9 further comprising one or more plug weights which fit within the one or more openings for forming plugs.

11. An apparatus for shaping a Platelet Rich Fibrin component of patient whole blood comprising:
    a main body further comprising a substantially planar surface wherein the main body has one or more openings therein for forming plugs of Platelet Rich Fibrin material;
    a reservoir positioned in the main body; and
    a plurality of channels fluidly connecting the substantially planar surface and the reservoir; and
    one or more plug weights which fit within the one or more openings for forming plugs, wherein the one or more plug weights is piston-shaped with a cylindrical portion and a rod portion, the rod portion sized to receive supplemental weights.

12. The apparatus for shaping a Platelet Rich Fibrin component of patient whole blood of claim 11 further comprising one or more sleeves sized to fit within the one or more openings for forming plugs, wherein a plug of a first dimension can be formed in the opening and a plug of a second, smaller dimension can be formed within a sleeve within an opening.

13. The apparatus for shaping a Platelet Rich Fibrin component of patient whole blood of claim 11 wherein the main body includes one or more bores for the one or more openings for forming plugs of Platelet Rich Fibrin material, the one or more bores for fluidly coupling the one or more openings for forming plugs to the reservoir within the main body.

14. The apparatus for shaping a Platelet Rich Fibrin component of patient whole blood of claim 11 wherein the main body includes a plurality of different-sized openings for forming plugs of Platelet Rich Fibrin material having different dimensions.

15. The apparatus for shaping a Platelet Rich Fibrin component of patient whole blood of claim 11 wherein the reservoir is positioned so that fluid in the reservoir is accessible without having to move another portion of the apparatus.

16. The apparatus for shaping a Platelet Rich Fibrin component of patient whole blood of claim 11 wherein the substantially planar surface is inclined toward the reservoir.

17. The apparatus for shaping a Platelet Rich Fibrin component of patient whole blood of claim 11 further comprising a lid that can be positioned above the main body at a plurality of distances.

18. The apparatus for shaping a Platelet Rich Fibrin component of patient whole blood of claim 11 wherein the one or more openings in the main body the main body has at least one bore therein that places the one or more openings in fluid communication with the reservoir.

19. The apparatus for shaping a Platelet Rich Fibrin component of patient whole blood of claim 11 further comprising a table stand removably attached to the main body, the table stand positioned to incline the main body and the channels and bores therein toward the reservoir in the main body.

* * * * *